United States Patent
Manassen et al.

(10) Patent No.: US 10,190,979 B2
(45) Date of Patent: Jan. 29, 2019

(54) METROLOGY IMAGING TARGETS HAVING REFLECTION-SYMMETRIC PAIRS OF REFLECTION-ASYMMETRIC STRUCTURES

(71) Applicant: KLA-Tencor Corporation, Milpitas, CA (US)

(72) Inventors: Amnon Manassen, Haifa (IL); Yuri Paskover, Caesarea (IL); Barry Loevsky, Yokneam Ilit (IL); Daria Negri, Nesher (IL)

(73) Assignee: KLA-Tencor Corporation, Milpitas, CA (US)

( * ) Notice: Subject to any disclaimer, the term of this patent is extended or adjusted under 35 U.S.C. 154(b) by 585 days.

(21) Appl. No.: 14/928,514

(22) Filed: Oct. 30, 2015

(65) Prior Publication Data

US 2016/0084758 A1 Mar. 24, 2016

Related U.S. Application Data

(63) Continuation of application No. PCT/US2014/058115, filed on Sep. 29, 2014.

(60) Provisional application No. 61/904,570, filed on Nov. 15, 2013.

(51) Int. Cl.
*G01N 21/47* (2006.01)
*G03F 7/20* (2006.01)
*G06F 17/50* (2006.01)

(52) U.S. Cl.
CPC ..... *G01N 21/4785* (2013.01); *G03F 7/70683* (2013.01); *G06F 17/5072* (2013.01)

(58) Field of Classification Search
CPC .................. G01N 21/4785; G03F 7/70683

USPC ............................................. 33/293; 702/108
See application file for complete search history.

(56) References Cited

U.S. PATENT DOCUMENTS

| | | | |
|---|---|---|---|
| 6,536,130 B1 | 3/2003 | Wu et al. | |
| 7,068,833 B1 * | 6/2006 | Ghinovker | G03F 7/70633 382/143 |
| 9,678,421 B2 * | 6/2017 | Levinski | G03F 1/42 |
| 9,739,702 B2 * | 8/2017 | Bringoltz | G01N 21/01 |
| 9,851,300 B1 * | 12/2017 | Bringoltz | G01N 21/55 |
| 9,946,167 B2 * | 4/2018 | Smilde | G03F 7/70633 |
| 9,958,791 B2 * | 5/2018 | Mathijssen | G03F 7/70683 |
| 2005/0084772 A1 | 4/2005 | Ballarin | |
| 2007/0291269 A1 | 12/2007 | Van der Schaar et al. | |

(Continued)

FOREIGN PATENT DOCUMENTS

TW 201324061 A 6/2013

OTHER PUBLICATIONS

TW Office Action dated Apr. 20, 2018 for Taiwan Patent Application No. 103133077.

*Primary Examiner* — Christopher W Fulton
(74) *Attorney, Agent, or Firm* — Suiter Swantz pc llo

(57) ABSTRACT

Metrology targets, design files, and design and production methods thereof are provided. Metrology targets comprising at least one reflection-symmetric pair of reflection-asymmetric structures are disclosed. The structures may or may not be periodic, may comprise a plurality of unevenly-spaced target elements, which may or may not be segmented. The asymmetry may be with respect to target element segmentation or structural dimensions. Also, target design files and metrology measurements of the various metrology targets are disclosed.

21 Claims, 6 Drawing Sheets

(56) References Cited

U.S. PATENT DOCUMENTS

| | | | |
|---|---|---|---|
| 2009/0224413 A1 | 9/2009 | Ghinovker | |
| 2013/0107259 A1 | 5/2013 | Choi et al. | |
| 2014/0136137 A1* | 5/2014 | Tarshish-Shapir | G06T 7/0004 |
| | | | 702/108 |
| 2015/0227061 A1* | 8/2015 | Tinnemans | G03F 9/7069 |
| | | | 355/53 |
| 2016/0161863 A1* | 6/2016 | Den Boef | G01B 11/24 |
| | | | 355/67 |
| 2016/0313654 A1* | 10/2016 | Zeng | G03F 7/70633 |
| 2017/0177760 A1* | 6/2017 | Socha | G01N 21/4785 |

* cited by examiner

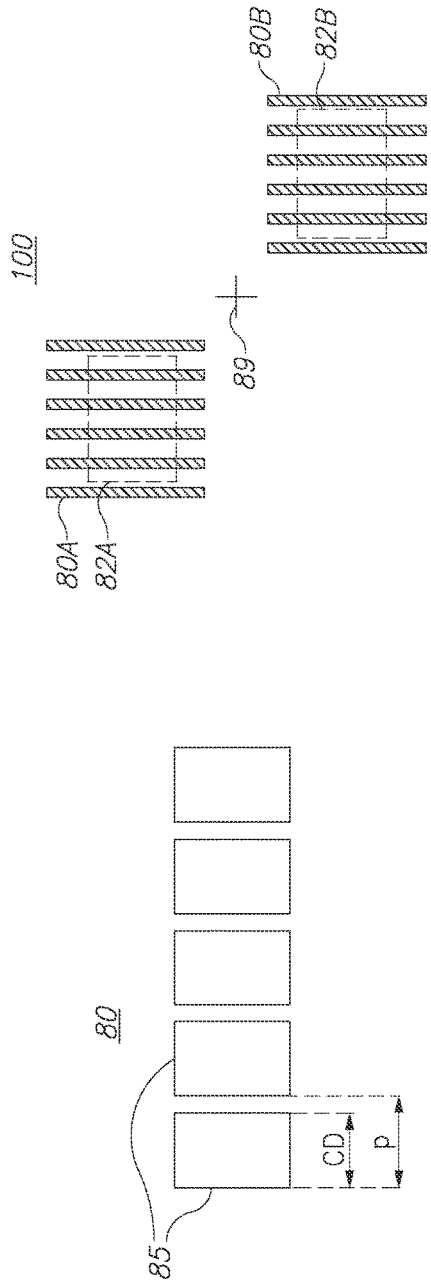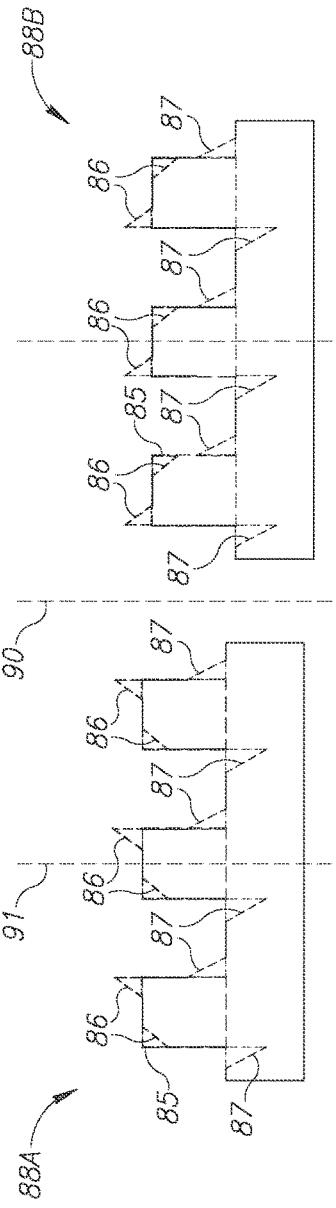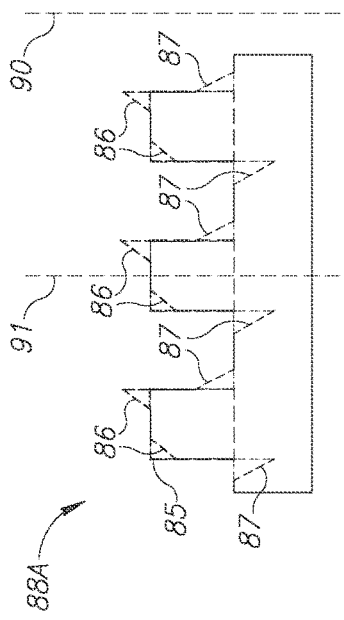

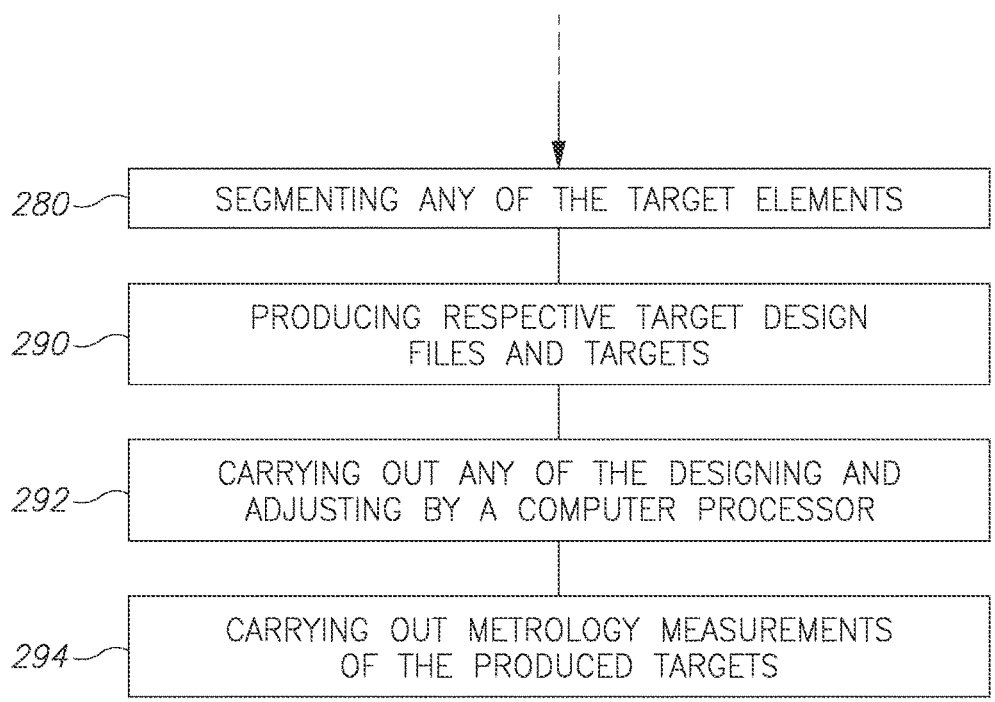
Figure 4 (cont. 1)

METROLOGY IMAGING TARGETS HAVING REFLECTION-SYMMETRIC PAIRS OF REFLECTION-ASYMMETRIC STRUCTURES

CROSS-REFERENCE TO RELATED APPLICATIONS

This application is filed under 35 U.S.C. § 111(a) and § 365(c) as a continuation of International Patent Application No. PCT/US14/58115, filed on Sep. 29, 2014, which application claims the benefit of U.S. Provisional Patent Application No. 61/904,570, filed on Nov. 15, 2013, which applications are incorporated herein by reference in their entireties.

TECHNICAL FIELD

The present invention relates to the field of metrology targets, and more particularly, to asymmetric imaging metrology targets.

BACKGROUND

Metrology targets are designed to enable the measurement of parameters that indicate the quality of wafer production steps and quantify the correspondence between design and implementation of structures on the wafer. Imaging metrology targets as specific structures optimize the requirements for device similarity and for optical image measurability and their images provide measurement data.

Typical target designs utilize inversion symmetry of the image printed at each layer. The images used for the overlay target are a box-in-box type of target, consisting of two or more concentric rectangles, each printed at a relevant process layer. Deviation from common center of symmetry of each of the rectangles is reported as overlay. Another method for the same purpose uses AIM (Advanced Imaging Metrology) targets, in which images used for overlay measurement are represented as a pair of gratings for each axis. The center of symmetry of each layer is determined by correlation of two gratings at each layer, separately for X and Y axes. Such targets allow for frequency filtering, reducing the effect of random noise on overlay calculation. Although AIM target possess multiple convenient features, as a periodic pattern that allows for convenient sub-pixel interpolation, and mathematical noise reduction, they often suffer from significant suppression of high harmonics by the optical system, leaving the image of virtually single frequency. In such a case displacement (overlay) and asymmetry of the target are indistinguishable and accurate overlay measurement cannot be verified.

Hence, in current AIM targets the frequencies observed in the image are dictated solely by the pitch (period) of the structure, as the relative phase and intensity of the harmonics are determined by the shape of the repetitive structure (generating feature). In particular, symmetric features, based on their extent and particular details of the light scattering, often exclude generation of particular diffraction orders, making image analysis algorithms rather vulnerable to errors.

SUMMARY OF THE INVENTION

The present invention comprises a metrology target having at least one reflection-symmetric pair of reflection-asymmetric structures having a reflection-asymmetry.

The present invention also comprises metrology measurements of a metrology target having at least one reflection symmetric pair of reflection-asymmetric structures.

The present invention also comprises a target design file for a metrology target having at least one reflection symmetric pair of reflection-asymmetric structures.

The present invention also comprises a method having the step of configuring an imaging target to have at least one reflection-symmetric pair of reflection-asymmetric structures.

The present invention also comprises a computer-based apparatus having a memory element configured to store a plurality of computer-readable instructions, and a processor configured to execute the plurality of computer-readable instructions to configure an imaging target to have at least one reflection-symmetric pair of reflection-asymmetric structures.

The targets comprise reflection-symmetric pair(s) of reflection-asymmetric structures. Each pair is reflection-symmetric with respect to a central reflection plane between the structures, while the structures themselves and/or the target elements from which the structures are composed are reflection-asymmetric with respect to a reflection plane through the middle of the structure or the target element, respectively. In an example embodiment, the structures may be not periodic, and comprise a plurality of unevenly-spaced and/or a plurality of reflection-asymmetric target elements. In an example embodiment, the structures may be periodic, and elements of the periodic structures may be asymmetric with respect to their dimensions. In an example embodiment, the target elements may be segmented.

Design and production methods may comprise designing, configuring and/or producing targets with the disclosed characteristics and features. The reflection asymmetry may be defined with respect to the target element segmentation. The predetermined reflection asymmetry enables measuring metrology parameters while overcoming uncontrolled inaccuracies which are not reflection-symmetric as the pair(s) of structures. Reflection asymmetry may be achieved by varying different parameters, such as target element dimensions, structure pitches and segmentation features.

These and other aspects, advantages and features of the present invention will be better appreciated by those having ordinary skill in the art in view of the following detailed description of the invention in view of the drawings.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 1A is a high level schematic illustration of a periodic structure having repetitive target elements which share common dimension (e.g., critical dimension—CD) and have a single pitch (P), according to the prior art;

FIG. 1B is a high level schematic illustration of an imaging target having a pair of periodic structures, positioned with respect to a center of symmetry;

FIG. 1C is a high level schematic illustration of symmetries and asymmetries in measured imaging signals with respect to designed periodic structures, according to some embodiments of the invention;

DETAILED DESCRIPTION OF THE INVENTION

Figure 1D:
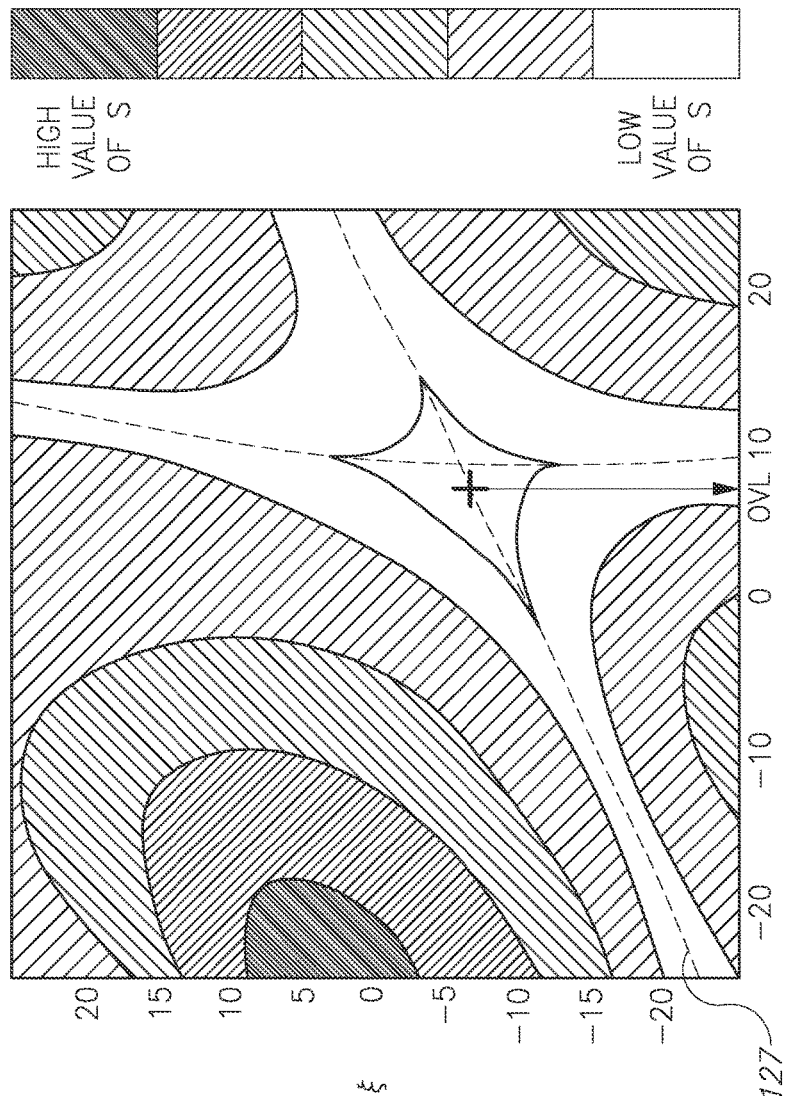
FIG. 1D is a high level schematic illustration of simulated overlay detection using a reflection-symmetric pair of reflection-asymmetric structures, according to some embodiments of the invention.

At the outset, it should be appreciated that like drawing numbers on different drawing views identify identical, or functionally similar, structural elements of the invention. While the present invention is described with respect to what is presently considered to be the preferred aspects, it is to be understood that the invention as claimed is not limited to the disclosed aspect. Also, it is to be understood that the invention is not limited in its application to the details of construction and the arrangement of the components set forth in the following description or illustrated in the drawings. The invention is applicable to other embodiments or of being practiced or carried out in various ways and is intended to include various modifications and equivalent arrangements within the spirit and scope of the appended claims.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

In the below description, an embodiment is an example or implementation of the invention. The various appearances of "one embodiment", "an embodiment", "certain embodiments" or "some embodiments" do not necessarily all refer to the same embodiments.

The terms "metrology target" or "target" as used herein in this application, are defined as structures designed or produced on a wafer which is used for metrological purposes.

The terms "target structure" or "structure" as used in this application refer to any kind of designed or produced structure in at least one layer of the target.

The term "target element" as used herein in this application, is defined as a feature in the metrology target such as individual target areas or boxes, grating bars, etc. Target elements may be full or empty (gaps), and may also be segmented, i.e., may comprise multiple smaller features which cumulatively constitute the target element. Target element segmentation may comprise two or more segments, which may be equal or unequal, repetitive or alternating. Structures may be characterized by different parameters such as sizes of target elements (e.g., critical dimension—CD) and spaces between target elements, as well as distances between elements and forms of the elements.

The term "pitch" as used in this application refers to the distances between structure elements even when the structures are not periodic, i.e., a non-periodic structure composed of several elements is referred to as having several pitches which signify the distances between the elements.

The term "periodic structure" as used in this application refers to any kind of designed or produced structure in at least one layer which exhibits some periodicity. The periodicity of periodic structures is characterized by their pitch, namely its spatial frequency. For example, a bar as a target element may be produced as a group of spaced parallel lines, thereby reducing the minimal feature size of the element and avoiding monotonous regions in the target. Each element of a periodic structure is referred to as a target element. Pitches of either or both periodic structures and segmented target elements may be constant or may vary along the respective structure or elements (see above).

The terms "reflection symmetry" and "reflection asymmetry" as used herein in this application, are defined with respect to respective reflection planes. Specifically, one reference reflection plane is located between two structures in a pair of structures and another reference reflection plane is located at the middle of a structure, both planes determined with respect to given regions of interest (ROIs)—i.e., the sides of each plane may undergo perpendicular translation to determine their symmetry or asymmetry, according to the target design.

Metrology of lithographic processes employs analysis of microscopic images of specially designed targets. The image analysis algorithms utilize harmonic analysis of the images, and symmetry considerations for calculation of relative displacement of the structures printed at different layers at various stages of the lithography process. Both proper harmonics content and proper symmetry of targets are required to ensure the accuracy of overlay measurements. The disclosed invention comprises target design types that optimize harmonic content of the images, taking into account symmetry conditions necessary to ensure high accuracy of algorithmic image analysis.

The present invention uses periodic or quasi-periodic sequences of asymmetric structures for imaging based optical lithography metrology. Since asymmetry cannot be achieved with a single harmonic, the information content of the disclosed targets is higher than that of standard AIM targets, allowing for higher accuracy of measurements, and enables the utilization of the deliberate asymmetry to decrease of measurement sensitivity to local variations in lithographic processes.

In the targets disclosed herein, the features of the AIM target structure are de-symmetrized, while the inversion symmetry requirement is maintained. Breaking the symmetry of specific features (using an asymmetric form as periodic pattern) avoids exclusion rules for diffraction orders, and thus prevent suppression of harmonics in the target image; ensures a well-defined symmetry of the left and right structures (e.g., gratings), with low sensitivity to random perturbations; and avoids false-symmetry centers, which allows for unique and accurate determination of the center of symmetry of target at each layer.

FIG. 1B is a high level schematic illustration of an imaging target 100 having a pair of periodic structures 80A and 80B positioned with respect to center of symmetry 89. The arrangement of the pair of periodic structures illustrated in FIG. 1B as well as prior art arrangements of such pairs may be used in some embodiments of the present invention with the disclosed pairs of modified structures 115, which may be periodic or not. Respective regions of interest (ROI's) 82A and 82B are defined in periodic structures 80A, 80B (or structures 115) from which an imaging signal is extracted. The exemplary imaging target and equivalent target patterns may be used with either prior art periodic structures 80 (shown in FIG. 1A) or with structures 115 according to some embodiments of the invention. Cross 89 represents the intersection of horizontal and vertical symmetry planes (for 180° rotations) of target 100. In the illustrated cases, the vertical symmetry plane coincides with reflection symmetry plane 90. Central pair reflection symmetry plane 90, center of symmetry 89, and central periodic element symmetry plane 90 may be defined with respect to ROI's 82A and 82B. The invention is not limited, however, to specific orientation and number of symmetry planes.

FIG. 1C is a high level schematic illustration of symmetries and asymmetries in structures 115 and in measured imaging signals with respect to designed structures, according to some embodiments of the invention. FIG. 1C illustrates schematically periodic structures and corresponding signal components 88A and 88B measured using respective ROI's 82A and 82B superposed on a cross section of actual periodic structures 80A, 80B.

Signals 88A and 88B are composed from baseline signal 85, reflection-symmetric signal 86, and reflection-asymmetric signal 87. Baseline signal 85 follows periodic structures 115. Reflection-symmetric signal 86 is symmetric with respect to reflection symmetry plane 90 of pair 110 of structures 115 (reflection plane 90 may be central between structures 115). Reflection-asymmetric signal 87 is asymmetric with respect to plane 90 and has, instead, a translational symmetry. Further denoted in FIG. 1C is reflection plane 91 going through the middle of periodic structure 115 or target element 105. Reflection-symmetric signal 86 may be designed into structure 115 (a component of signal 86 may also arise unintentionally).

Reflection-asymmetric signal 87 is due to uncontrolled process inaccuracies, such as inaccuracies arising from the Chemical Mechanical Polishing/Planarization (CMP) process, which are inherently translation-symmetric and reflection-asymmetric. In the present invention, reflection-symmetric signal 86 is enhanced by appropriate configuration of structures in a way that provides more accurate measurement of metrology parameters such as overlay. FIG. 1C is understood to qualitatively illustrate both signals 85, 86, 87 (see derivation below) and corresponding structures 115 which are designed to generate the specified signal features. Structures 115 are not limited to illustrated periodic structures 88A, 88B and their illustrated modifications.

The specific symmetric signal 86, and respective structures 115 may be designed according to the following considerations. ROI 82A, 82B is denoted by $\xi$, the measured kernels are denoted by $K_1$, $K_2$ (corresponding to signal components 88A, 88B respectively). Symmetrizing the problem with respect to ROI choice $\xi$ is carried out by defining $F_1$ and $F_2$ as symmetrized functions corresponding to $K_1$, $K_2$, respectively, namely:

$$F_1 = K_1(x-\xi) + K_1(-x-\xi); \text{ and}$$

$$F_2 = K_2(x+\xi-\Delta+\delta) + K_2(-x+\xi-\Delta+\delta),$$

with x being a free variable, $\Delta$ being the shift between structures 115 and $\delta$ being the overlay (to be measured).

Overlay $\delta$ may be found by minimizing the distance function:

$$s(\delta, \xi) = \int dx |F_1 - F_2|^2. \qquad \text{Equation 1}$$

In particular, a global minimum for S should exist in order for an unambiguous overlay $\delta$ to be extracted. Applying a harmonic expansion and substituting $\Delta' = \Delta - \delta$, the expression $F_1 - F_2$ in Equation 1 becomes:

$$F_1 - F_2 = \sum_k \cos(kx) \cdot \left\{ g_k \sin k\left(\xi - \frac{\Delta'}{2}\right) \sin k\frac{\Delta'}{2} + r_k \cos k\left(\xi - \frac{\Delta'}{2}\right) \sin k\frac{\Delta'}{2} + t_k \sin k\left(\xi - \frac{\Delta'}{2}\right) \cos k\frac{\Delta'}{2} \right\}$$

$$= \text{signal}(g)85 + \text{signal}(r)86 + \text{signal}(t)87$$

wherein signals 85, 86, 87 are schematically represented by their symmetry features in FIG. 1C.

$$\text{Signal}(g)85 = \Sigma_k \cos(kx) \cdot g_k \sin k\left(\xi - \frac{\Delta'}{2}\right) \sin k\frac{\Delta'}{2}$$

represents periodic structure such as 88A, 88B (with respect to ROIs 82A, 82B) which are symmetric with respect to plane 91, $$\text{Signal}(r)86 = \Sigma_k \cos(kx) \cdot r_k \cos k\left(\xi - \frac{\Delta'}{2}\right) \sin k\frac{\Delta'}{2}$$

represents the disclosed asymmetry introduced into structures 115, which is asymmetric with respect to plane 91 but symmetric with respect to plane 90, i.e., pair 110 of structures 115 having signal 86 is reflection symmetric.

$$\text{Signal}(t)87 = \Sigma_k \cos(kx) \cdot t_k \sin k\left(\xi - \frac{\Delta'}{2}\right) \cos k\frac{\Delta'}{2}$$

represents uncontrolled asymmetric inaccuracy, which may be overcome by configuring structures 115 to comprise signal 86. It is noted that the introduction of reflection asymmetric signal (r) 86 provides the single global maximum of the function $S(\delta, \xi)$ by being positive (>0) when signal (g) 85 and signal (t) 87 are zero (e.g., at $$\left(\text{e.g., at } k\left(\xi - \frac{\Delta'}{2}\right) = 0\right).$$

Signal 86 may thus be configured into structures 115 (originally equivalent to signal 85) to yield a measurement signal that overcomes the inaccuracy introduced by uncontrolled signal 87. According to similar principles, the disclosed invention further comprises extending structure design to comprise additional harmonies, beyond those stated above. The measurement algorithm may further comprise compensation for optical asymmetries (TIS) which may result in unequal modifications of structures 115 in symmetric pairs 110.

FIG. 1D is a high level schematic illustration of simulated overlay detection using a reflection-symmetric pair of reflection-asymmetric structures, according to some embodiments of the invention. FIG. 1D depicts a typical topographic map of $\int(S(x, \xi, \Delta))^2 dx$, the global minimum of which provides the required overlay δ. It is noted that the term denoted as $$\text{signal}(r)86 = \Sigma_k \cos(kx) \cdot r_k \cos k\left(\xi - \frac{\Delta'}{2}\right) \sin k\frac{\Delta'}{2}$$

is the term that transforms trough 127 from having multiple minima (without signal r) to having a single global minimum, which is marked by a cross in FIG. 1D. The value of δ for this minimum indicates the resulting overlay (marked OVL on the map). FIG. 1D is to be understood as a non-limiting illustrative simulation result. The inventors have run simulations of many variations of structures 115 and respective measurement conditions to adjust structures 115 to required levels of detection and accuracy, according to the disclosed principles.

Figure 2A:
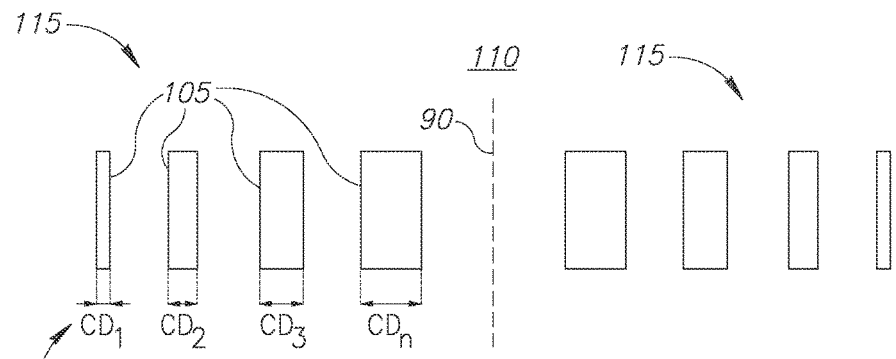
FIG. 2A is a high level schematic illustration of periodic structures and target elements thereof, according to some embodiments of the invention.
Figure 2B:
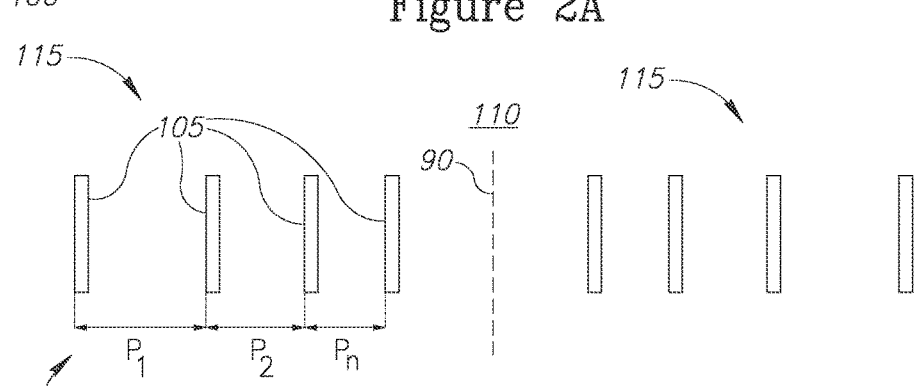
FIG. 2B is a high level schematic illustration of periodic structures and target elements thereof, according to some embodiments of the invention.
Figure 2C:
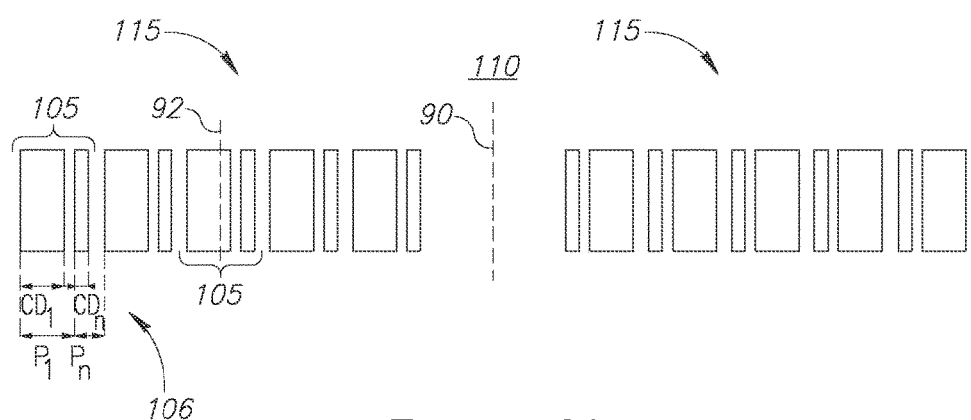
FIG. 2C is a high level schematic illustration of periodic structures and target elements thereof, according to some embodiments of the invention.

FIGS. 2A-2C are high level schematic non-limiting illustrations of structures 115 and target elements 105 thereof, according to some embodiments of the invention. The disclosed invention comprises metrology targets comprising at least one pair 110 of structures 115. Pair 110 is reflection-symmetric (with respect to plane 90) while either or both structures 115 and target elements 105 thereof are reflection-asymmetric (with respect to plane 91—see FIG. 1C—and/or plane 92—see FIG. 2C—respectively). The asymmetry of structures 115 and/or of target elements 105 may be expressed in a range of dimensions and/or features 106, which may comprise target element dimensions such as critical dimension (CD), structure pitches (i.e., distances between elements), target element segmentation, etc. In the illustrated non-limiting examples, varying target elements CD's are denoted as $CD_{1...n}$ (FIG. 2A), varying structure pitches (distances between elements) are denoted as $p_{1...n}$ (FIG. 2B), and varying target element segmentation is denoted as combination of $CD_{1...n}$ and $p_{1...n}$ relating to each target element 105 (FIG. 2C). FIG. 2C also illustrates a reflection plane 92 of single target element 105 to show the reflection asymmetry of target element 105 (reflection plane 91 of structure 115 coincides with illustrated reflection plane 92 so that the reflection asymmetry of structure 115 is evident as well). Clearly, variation in any parameter 106 may be alternating or periodic. In any of the designs, pair(s) 110 of structures 115 may be designed to be reflection symmetric with respect to plane 90, i.e., the asymmetric structures 115 and/or target elements 105 are reflected in the respective pair member.

Figure 3:
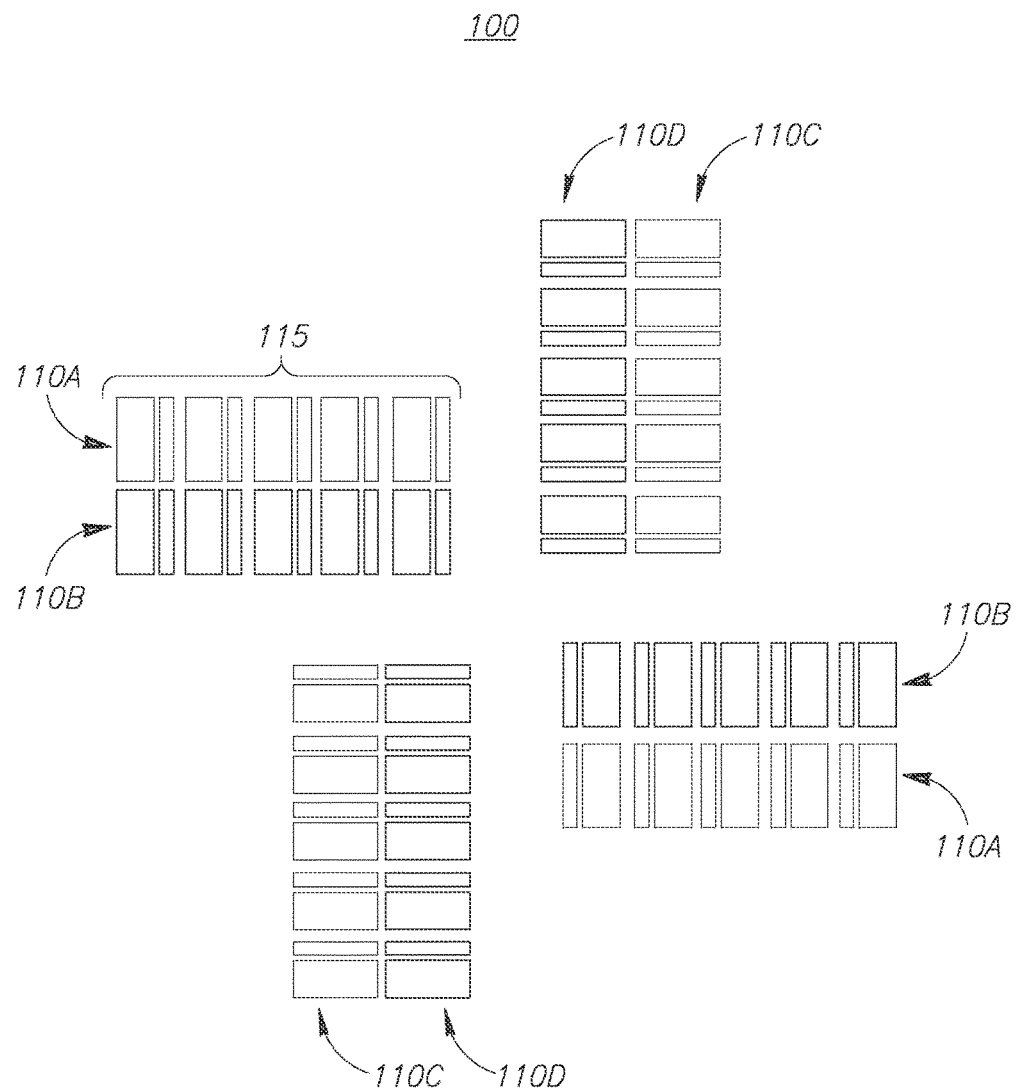
FIG. 3 is a high level schematic illustration of two dimensional targets having symmetric pairs of asymmetric periodic structures, according to some embodiments of the invention; and, FIG. 4 is a high level flowchart illustrating a method, according to some embodiments of the invention.

FIG. 3 is a high level schematic illustration of two dimensional targets 100 having symmetric pairs 110A-D of asymmetric structures 115, according to some embodiments of the invention. Any of designed targets 100 may be extended into two dimensional targets 100, having the same or different target structure pairs 110A-D in each measurement direction. In the illustrated example, two symmetric pairs 110A, 110B of asymmetric structures 115 are designed in the X measurement direction and two symmetric pairs 110C, 110D of asymmetric structures 115 are designed in the Y measurement direction. Any permutation of asymmetric structures 115 may be used in any of pairs 110A-D.

In target 100, any of the following design principles may be applied: structures 115 may be asymmetric with respect to their pitch (distances between elements constant or varying); structures 115 may be asymmetric with respect to their dimensions; target elements 105 may be segmented and wherein the reflection asymmetry may be designed with respect to the target element segmentation. In any case, the reflection-asymmetry may be configured to be distinguishable over measurement inaccuracies. The disclosed invention further comprises target design files of any of disclosed metrology targets 100 as well as metrology measurements of any of disclosed metrology targets 100.

In certain embodiments, reflection-asymmetric structures 115 may be designed in a way that is least sensitive to process errors. Furthermore, reflection-asymmetries may be selected to avoid amplification of process errors and/or optical asymmetries which may result in enhanced algorithmic inaccuracies. Design methods may thus further comprise (using simulations or produced targets) checking the fidelity of overlay calculation versus process errors; checking the fidelity of the algorithm in face of optical asymmetries as aberrations. Specific designs may be compared with respect to the contrast-focus curves they yield and the resulting precision characteristics. The designs may be evaluated according to different parameters, such as tool induced shift (TIS) and overlay (OVL) inaccuracy.

In certain embodiments, target designs may further be adapted to reduce their sensitivity to random errors and process variations. Random process errors effects may be simulated as random noise on the image with typical amplitude of up to ~1% of that of the significant harmonic and correlation distance of up to half pitch. Shot noise may be simulated as zero correlation random addition with RMS ~2.5% (5 out of 200 gray levels). Structure asymmetry in targets 100 as reflected in signal (r) 86 may be configured to be measureable under addition of such or other noise characteristics.

Figure 4:
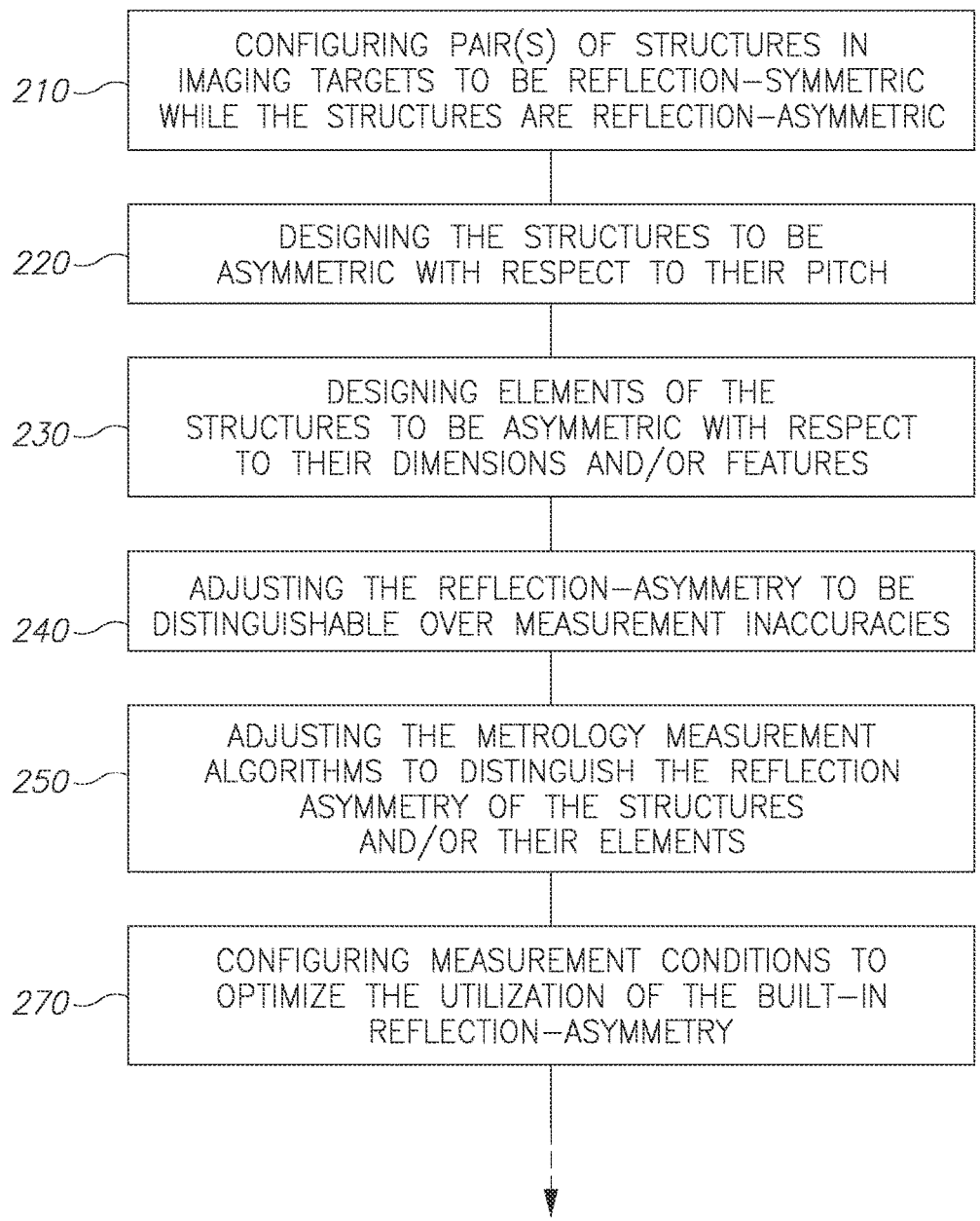

FIG. 4 is a high level flowchart illustrating a method 200, according to some embodiments of the invention. Method 200 may comprise stages for designing and/or producing targets 100, as well as configuring respective target design files. Method 200 may further comprise measurement stages of targets 100. Method 200 may comprise any of the following stages, irrespective of their order.

Method 200 comprises configuring at least one pair of structures in an imaging target to be reflection-symmetric while at least one of the structures in the at least one pair and target elements of the structures are reflection-asymmetric (stage 210). For example, method 200 may comprise designing the structures to be asymmetric with respect to their pitch (stage 220); designing elements of the structures to be asymmetric with respect to their dimensions and/or features (stage 230); and/or segmenting target elements of the structures (stage 280) and adjusting the reflection asymmetry with respect to the target element segmentation.

Method 200 further comprises adjusting the reflection-asymmetry to be distinguishable over measurement inaccuracies (stage 240) and/or adjusting metrology measurement algorithms to distinguish the reflection asymmetry of the at least one of the structures and target elements thereof (stage 250) and/or configuring measurement conditions to optimize a utilization of the built-in reflection-asymmetry (stage 270).

Method 200 may further comprise producing respective target design files or targets (stage 290) and/or producing respective targets and carrying out metrology measurements of the produced targets (stage 294). Certain embodiments further comprise target design files and/or targets designed according to method 200.

Method 200 may further comprise carrying out any of the configuring, the adjusting and the designing and adjusting by a computer processor (stage 292). Certain embodiments further comprise a computer program product comprising a computer readable storage medium having computer readable program embodied therewith, the computer readable program configured to carry out any of the stages of method 200.

The invention is not limited to those diagrams or to the corresponding descriptions. For example, flow need not move through each illustrated box or state, or in exactly the same order as illustrated and described.

Thus, it is seen that the objects of the present invention are efficiently obtained, although modifications and changes to the invention should be readily apparent to those having ordinary skill in the art, for which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention as claimed.

What is claimed is:

1. A metrology target comprising:
   at least one reflection-symmetric pair of structures, wherein the at least one reflection-symmetric pair includes a first reflection-asymmetric structure and at least an additional reflection-asymmetric structure, wherein at least one of the first reflection-asymmetric structure or the at least an additional reflection-asymmetric structure includes a series of periodically spaced target elements, wherein at least some of the periodically spaced target elements are reflection-asymmetric.

2. The metrology target of claim 1, wherein the reflection-asymmetric target elements are segmented.

3. The metrology target of claim 2, wherein the reflection-asymmetry is with respect to the target element segmentation.

4. The metrology target of claim 1, wherein the target elements of the periodic structures have a dimension and are asymmetric with respect to the dimension.

5. The metrology target of claim 1, wherein the reflection-asymmetry is configured to be distinguishable over measurement inaccuracies.

6. A metrology method, comprising the step of:
   forming an imaging target to include at least one reflection-symmetric pair of structures, wherein the at least one reflection-symmetric pair includes a first reflection-asymmetric structure and at least an additional reflection-asymmetric structure, wherein at least one of the first reflection-asymmetric structure or the at least an additional reflection-asymmetric structure includes a series of periodically spaced target elements, wherein at least some of the periodically spaced target elements are reflection-asymmetric.

7. The method of claim 6, further comprising the step of:
   adjusting metrology measurement algorithms to distinguish a first reflection-asymmetry of the at least one of the first reflection-asymmetric structure or the at least an additional reflection-asymmetric structure and target elements thereof.

8. The method of claim 6, further comprising the step of:
   adjusting metrology measurement algorithms to distinguish the reflection-asymmetry of the at least one of the first reflection-asymmetric structure or the at least an additional reflection-asymmetric structure and target elements thereof.

9. The method of claim 6, wherein the periodic target elements have a dimension, and the method further comprises the step of:
   forming the target elements to be asymmetric with respect to the dimension.

10. The method of claim 9, wherein the dimension is structure pitch.

11. The method of claim 6, wherein the periodic target elements have a plurality of dimensions, and the method further comprises the step of:
    forming the target elements to be asymmetric with respect to at least one of the plurality of dimensions.

12. The method of claim 6, further comprising the step of:
    segmenting one or more of the target elements of at least one of the first reflection-asymmetric structure or the at least an additional reflection-asymmetric structure.

13. The method of claim 12, wherein the at least one of the first reflection-asymmetric structure or the at least an additional reflection-asymmetric structure are asymmetric with respect to the target element segmentation.

14. The method of claim 6, wherein the at least one of the first reflection-asymmetric structure or the at least an additional reflection-asymmetric structure have reflection-asymmetry, and the method further comprising the step of:
    adjusting the reflection-asymmetry to be distinguishable over measurement inaccuracies.

15. The method of claim 6, further comprising the step of:
    adjusting metrology measurement algorithms to distinguish the reflection asymmetry of the at least one of the first reflection-asymmetric structure or the at least an additional reflection-asymmetric structure and target elements thereof.

16. The method of claim 6, further comprising the step of:
    performing metrology measurements of the formed targets.

17. An apparatus, comprising:
    a memory element configured to store a plurality of computer-readable instructions; and
    a processor configured to execute the plurality of computer-readable instructions to:
    configure an imaging target to include at least one reflection-symmetric pair of structures, wherein the at least one reflection-symmetric pair includes a first reflection-asymmetric structure and at least an additional reflection-asymmetric structure, wherein at least one of the first reflection-asymmetric structure or the at least an additional reflection-asymmetric structure includes a series of periodically spaced target elements, wherein at least some of the periodically spaced target elements are reflection-asymmetric.

18. A metrology target comprising:
    at least one reflection-symmetric pair of structures, wherein the at least one reflection-symmetric pair includes a first reflection-asymmetric structure and at least an additional reflection-asymmetric structure, wherein at least one of the first reflection-asymmetric structure or the at least an additional reflection-asymmetric structure includes a series of non-periodic target elements.

19. A metrology target comprising:
    at least one reflection-symmetric pair of structures, wherein the at least one reflection-symmetric pair includes a first reflection-asymmetric structure and at least an additional reflection-asymmetric structure, wherein at least one of the first reflection-asymmetric structure or the at least an additional reflection-asymmetric structure includes a series of unevenly-spaced target elements.

20. The metrology target of claim 19, wherein the unevenly-spaced target elements are segmented.

21. The metrology target of claim 20, wherein the reflection-asymmetry is with respect to the target element segmentation.

* * * * *